United States Patent [19]

Uson

[11] 4,009,711
[45] Mar. 1, 1977

[54] PENILE PROSTHESIS FOR THE MANAGEMENT OF ERECTILE IMPOTENCE

[76] Inventor: Aurelio C. Uson, 225 Maple St., Englewood, Bergen County, N.J. 07631

[22] Filed: Mar. 17, 1976

[21] Appl. No.: 667,532

[52] U.S. Cl. .......................................... 128/79; 3/1
[51] Int. Cl.² .......................................... A61F 5/00
[58] Field of Search ............... 128/79, 92 R, 303 R; 3/1

[56] References Cited

UNITED STATES PATENTS

| | | | |
|---|---|---|---|
| 3,853,122 | 12/1974 | Strauch et al. | 128/79 |
| 3,954,102 | 5/1976 | Buuck | 128/79 |

*Primary Examiner*—Lawrence W. Trapp
*Attorney, Agent, or Firm*—Anthony J. Casella

[57] ABSTRACT

A penile prosthesis which is adapted for the treatment of erectile impotence is surgically implanted in a man and includes two elongated body portions, each adapted to be surgically implanted in a corpus cavernosum of the penis, with each body portion including a non-distensible portion made of a semi-rigid silastic material and adapted to be implanted into the root end of the corpus cavernosum, and a distensible body portion formed unitary with said non-distensible portion, with the distensible body portion adapted to be surgically implanted into the tunica end of said corpus cavernosum. Each distensible body portion is connected by tubing to a fluid reservoir surgically implanted in the scrotal sac. Suitable valve means are provided for controlling the flow of fluid between said fluid reservoir and said distensible body portions.

13 Claims, 4 Drawing Figures

U.S. Patent  Mar. 1, 1977  4,009,711
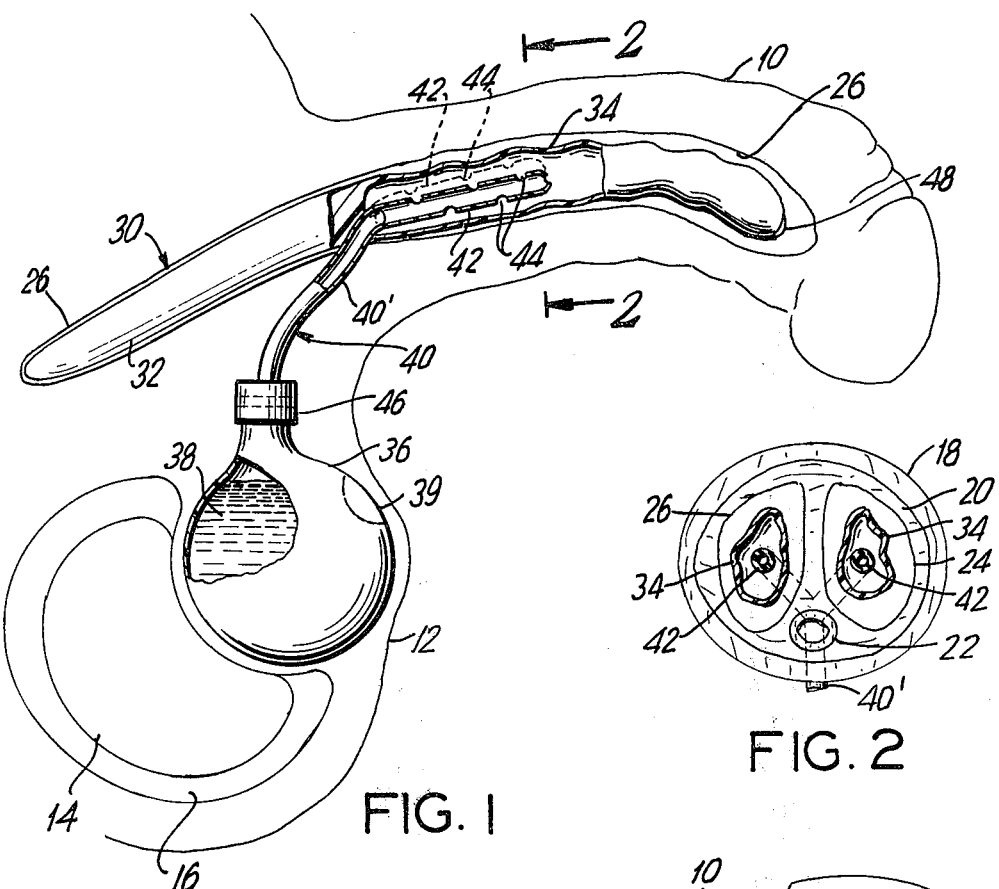
FIG. 1
FIG. 2
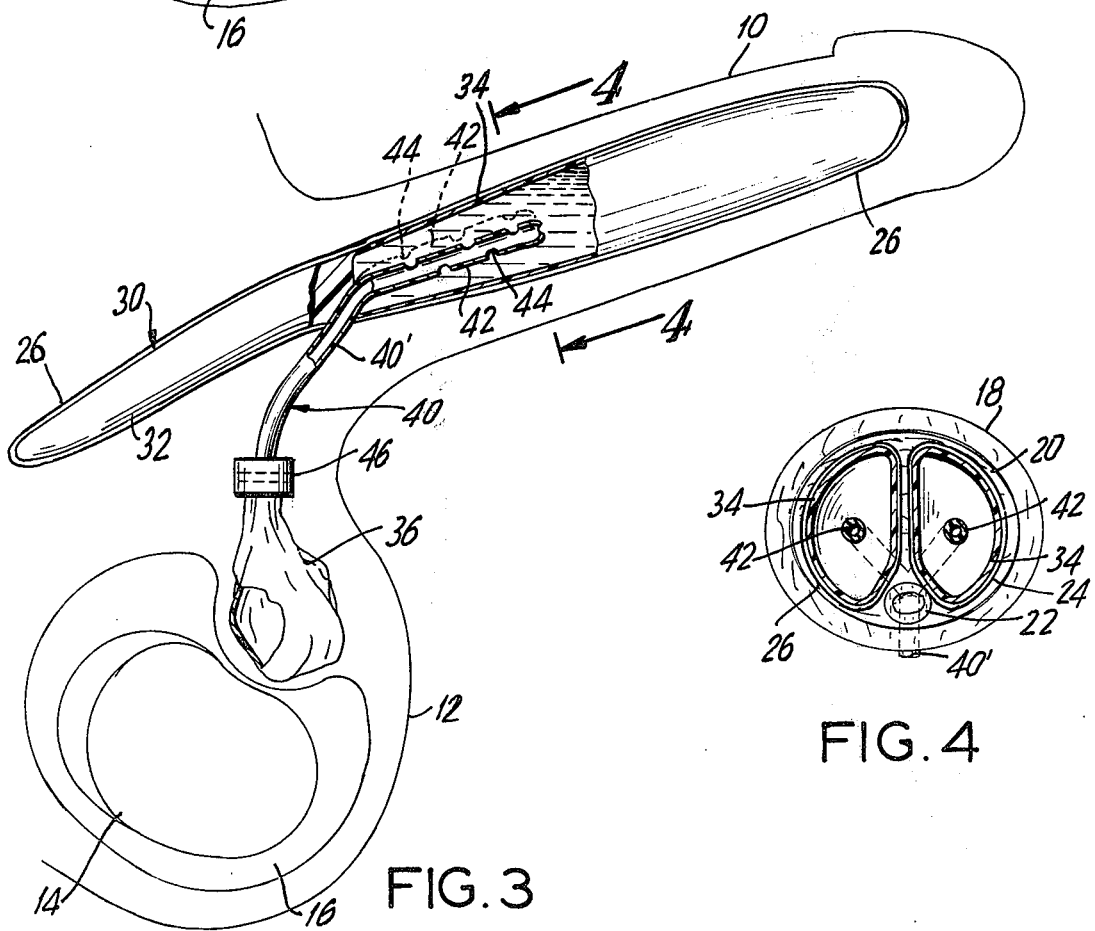
FIG. 3
FIG. 4

PENILE PROSTHESIS FOR THE MANAGEMENT OF ERECTILE IMPOTENCE

Electile penile impotence results from various functional and organic causes. Its management has always been a difficult problem to urologists and other physicians. Adequate evaluation of the impotent man must include endocrine studies, psychiatric counseling and complete urological examination. However, if the patient has an organic type of erectile impotence or does not respond to psychiatric, endocrine or urological therapy, the physician may then consider surgical implantation of a penile prosthesis.

There are several penile prostheses known in the art. A first prosthesis is a single and simple "rod like" device adapted to be implanted in between the corpora cavernosa of the penis under the Buck's fascia. It is made of a suitable semi-rigid elastomeric material, such as silicone rubber.

One of the problems usually encountered with this known prosthesis is that it does not afford consistently a good penile stability and rigidity for adequate sexual intercourse. Another problem with this "rod gentle prosthesis stems from the fact that if it is not properly implanted well under the pubic bone, the penis may buckle at its base, and thus will make sexual intercourse impossible or very uncomfortable. In addition, since the prosthesis is of a rigid type, the penis is maintained in a permanent state of erection. This may create cosmetic difficulties as well as psychological problems to the patient, and occasionally, penile discomfort. Furthermore, if the prosthesis is not properly implanted between the corpora, it may erode through the urethra or through the glans penis causing infection, pain and much trouble to the patient, including further surgery. Finally, there have been cases where the prosthesis has been accidentally broken, thereby creating great discomfort and frustration to the bearer, and also requiring supplementary surgery.

A second type of known penile prosthesis consists of a "rod like" body with a silicone sponge interior, encased in a firmer silicone coat. The tail end of this prosthesis is slightly more rigid than the body. The prosthesis is implanted in pairs, one prosthesis within each corpus cavernosum of the penis. This prosthesis usually gives a satisfactory penile erection for adequate intercourse. However, being of the rigid type, the prosthesis gives a permanent penile erection with occasional mild penile discomfort and, at times, psychological embarrassment to the patient who engages in active sports.

Another known prosthesis in the art is the so-called inflatable penile prosthesis which is a relatively complex apparatus. Essentially, it consists of two distensible and fairly long "finger like" bodies that are surgically inserted within the corpora cavernosa. From each distensible body there extends a long and flexible conduit going to a fluid reservoir that is placed in the lower abdomen under the fat pad and above the stomach muscles. From this reservoir four additional tubes extend of two pumping devices (two tubes to each pumping device) implanted in the upper scrotum; one on each side. The need for placing the larger reservoir in the lower abdomen stems from the fact that each body of the penile prosthesis is inflatable in its entire length, and accordingly, a substantial amount of fluid is required, usually on the order of 30 to 40 cubic centimeters for each inflatable body. Furthermore, interposed in each of the four tubes is a suitable valve (a total of 4 valves) which allows the flow of water or fluid in one direction or another depending on whether the patient desires to have a penile erection or a detumescence. Because of the four tiny and complex valves which this prosthesis requires to operate and because of the bulky fluid reservoir, the length and number of the connecting tubes traveling from the penis to the midabdomen and from there to the scrotum where the two pumping devices are placed, plus the two very delicate elongated inflatable penile prostheses, it is possible that this complex mechanism may malfunction at one point or another, failing thereby to achieve its intended purpose with great frustration to the patient. In addition, this malfunction would require further surgery and extra parts for the replacement of the jammed component or components. In view of the complexities and potential complications inherent in this prosthetic device, as well as the extensive and meticulous surgery which is required for its correct implantation, the practical use of this prosthesis is limited. An additional shortcoming of this prosthetic device is its relatively high cost, plus the high costs associated with hospitalization and the surgeon's fee, thereby making its clinical application almost prohibitive.

The prosthesis of the subject invention overcomes the shortcomings of the prior art. Its principal objectives are to provide a more comfortable, simpler, cosmetically pleasing, reasonably priced and highly efficient mechanical device for the management of penile erectile impotence.

It is a primary and essential feature of the subject invention to provide a prosthesis which has the benefits of being both in part semi-rigid and in part inflatable, particularly, where such features are most desirable, i.e. rigid at the root of the penis and inflatable at the pendulous portion of the penis.

Another important feature of the subject invention is the simple construction and compact assemblage of the entire prosthesis with hardly any possibility left for malfunction. Still, other additional features are its reduced price, particularly; when compared with the "all inflatable prosthesis" of the prior art and its simplicity in the surgical implantation, minimizing the potential problems which are usually associated with other prostheses.

In general, the subject penile erectile prosthesis comprises a body member having a non-distensible portion and a distensible body portion, with the latter being connected by suitable conduit means to a fluid supply source, and valve means being provided to control the flow of fluid between the distensible portion and the fluid supply means. The non-distensible portion is preferably made of plastic material, such as Silastic, which is semi rigid, and is adapted to be implanted into the root end of the corpus cavernosum of a penis. The distensible body portion is preferably formed unitary with said non-distensible portion, an is surgically implanted into the tunica end of the corpus cavernosum. Two such body members are provided, one for each corpus cavernosum, with each of the distensible body portions being connected by suitable conduits, including valve means, which extend to the fluid reservoir preferably surgically implanted in the scrotal sac.

More specifically, the subject penile prosthesis includes:

1. An elongated body which is distensible and comprises the distal ⅔ of the penile prosthesis.
2. A cylindrical or "tail-like" part with a tapering end which is semi-rigid and non-distensible and comprises the proximal ⅓ of the prosthesis.

These two components No. 1 and No. 2 are united or bonded together to make a single unit and as such, is implanted surgically into each corpus cavernosum of the penis.

3. A connecting conduit or tube which goes from inside each distensible body of the prosthesis, to the underlying fluid containing reservoir.
4. A "ball like" fluid reservoir which also serves as a pumping device comprises the 4th component of this prosthesis.
5. A suitable valve which is interposed between the connecting tube and the neck of the fluid reservoir, constitutes the 5th and last component of this prosthesis.

While components No. 3 and No. 4 and No. 5 are usually implanted through the same perineal incision as components No. 1 and No. 2, they are positioned as follows: No. 5 and No. 4 in the upper scrotum and No. 3 in the perineal structures, between the upper scrotal compartment and the crura of the penis.

The material which can be used for the construction of all parts or components of the subject prosthesis must, of course, be non-reactive, non-toxic and well tolerated by the adjacent organic tissues. In addition, it must be resistent to the usual wear and tear and remain "healthy" and functional with the passage of time. All these requirements are met by medical grade silicone rubber.

Specific details relative to the subject invention will be fully described below with reference to the accompanying drawings in which:

FIG. 1 is a partial sectional view of the subject penile prosthesis in a deflated condition as surgically implanted in a male wherein the penis is in a semi-flaccid state;

FIG. 2 is a cross-sectional view taken along line 2—2 in FIG. 1;

FIG. 3 is a view similar to FIG. 1 except that the prosthesis is fully inflated;

FIG. 4 is a view taken along line 4—4 in FIG. 3.

FIG. 1 shows a sagital view of a penis 10, scrotal sac 12 which carries testicles 14 and tunica vaginalis 16. As illustrated in FIG. 2, the penis 10 includes a skin surface 18, Buck's fascia 20, the urethra 22, and two corpus cavernosum, designated by the numerals 24 and 26.

As shown in FIGS. 1 through 4, penile prosthesis 30 basically comprises a semi-rigid non-distensible portion or tail 32 which is preferably formed unitary with an inflatable or distensible body portion 34, with the distensible body portion in communication with a fluid supply means. The latter includes a reservoir 36 that is surgically implanted in the scrotal sac 12, and which contains a suitable fluid 38 such as distilled water, with the reservoir 36 being connected to the distensible body portion 34 by a conduit 40, a portion 42 of which extends into the distensible portion 34 and includes a plurality of apertures 44. For controlling the flow of fluid between the reservoir and the distensible portion 34, suitable valve means 46 are provided which allows the flow in one way or another, and as the patient may desire. Thus, all the components of this prosthetic device such as the semi-rigid tail 32, the distensible body 34, the connecting tubes 40 and 42, the valve 46, and the reservoir 36, constitute a compact unit which can be assembled with ease and implanted surgically without difficulties and through one incision. The complete device consists of two penile prostheses 30, one for each corpus cavernosum, two connecting tubes 40, one for each prosthesis 30, two valves 46, one for each prosthesis 30, and two reservoirs 36, one for each unit. The prosthetic device can be simplified by eliminating one reservoir 36, and one valve 46. In this case, a Y-type of connecting tube 40' is used to join the reservoir with both distensible bodies 34, of the penile prosthesis 30, as shown in FIGS. 2 and 4.

Each non-distensible portion 32 of the penile prosthesis is semi-rigid and made of a plastic material such as silicone. This "tail-like" part of the prosthesis is surgically implanted at the root of each corpus cavernosum well under the puboischiatic rami. The distensible or inflatable bodies 34 have very thin walls, and are also made of silicone. They have an elongated configuration and are inserted within the tunica of the corpora cavernosa all the way up to the glans penis. To facilitate this maneuver at the tip of each distensible body a perforated patch 48 of silicone can be supplied, through which a fine thread of silk can be passed and exteriorized with the aid of a needle through the upper surface of the glans penis. By pulling gently on this thread of silk from the outside the prosthesis can be introduced all the way into the cropus cavernosum.

The fluid reservoir 36, which also functions as a pumping device, is spherical or pear shaped and it is easily implanted in the upper part of the scrotal sac 12. The capacity of this reservoir may vary from 20–30 c.c. or from 50–60 c.c. depending on whether two or one reservoirs are used. The walls of the reservoir are thin and elastic. Furthermore, they can be compressed easily by gentle squeezing with two or more fingers from the outside of the scrotum 12, in order to provide sufficient pressure for forcing fluid 38, through the valve 46, and through the conduit 40 into the distensible body portion 34.

If desired, at the surface of the reservoir there may be provided a small addible 39, which is designed for easier location and safe refilling of the fluid content as required. It is suggested that by merely puncturing the scrotal wall 12 and the addible 39 with a fine hypodermic needle attached to a syringe, additional fluid 38 may be injected into the reservoir 36.

The valve means 46, interposed between the reservoir and the fluid conduit 42 may also be made of silicone and constructed as a flap valve, ball valve, ring valve or any other suitable type.

A penile erection as provoked by the filling of the distensible body of the properly implanted prosthesis of the subject invention, is illustrated in FIGS. 3 and 4. As already indicated above, by gentile squeezing of the reservoir 36, fluid 38 is pumped through the valve 46 into the conduit 40 and transferred into each distensible body portion 34 until such time as the penis has a strong erection for adequate sexual intercourse. Following intercourse, it is merely necessary for the man to squeeze gently with two fingers the valve 46 from the outside, in order to drain the pressurized fluid from the distended portions of the penile prosthesis 34, back into the empty reservoir 36. This maneuver can be facilitated if the penis is also squeezed manually while the valve is maintained opened with the other hand. Once this part has been completed, the penis will become flaccid as is the case in any normal man after sexual intercourse, so that these patients can engage in all sorts of sports and activities without the fear of embarrassment.

Accordingly, a new and improved prosthesis for the management of erectile penile impotence is provided. This prosthesis can be easily manufactured, readily assembled, and surgically implanted without difficulty. Furthermore, due to its structural and functional simplicity, it is expected that potential complications will be minimal. Other advantages of the subject penile prosthesis when compared with prior art devices include: the small size of the reservoir 36, the use of one valve only 46, (maximum two valves) and a very short conduit 40. Furthermore, the subject prosthesis has a solid "tail-like" portion 32, which provides increased stability when the penis becomes erected, while it decreases considerably the volume of fluid needed for an adequate erection.

The subject prosthetic device as has been described and illustrated as being made of silicone. However, it will be realized that other suitable materials may also be used.

To those skilled in the art to which this invention relates, many changes in constructions and widely different embodiments and applications of the subject device will suggest themselves without departing from the spirit and scope of the invention. The disclosures and descriptions herein are purely illustrative and are not intended to be in any sense limiting.

What is claimed is:

1. A prosthesis for the treatment of penile erectile impotence comprising: a non-distensible portion adapted to be surgically implanted into the root end of a corpus cavernosum of a penis; a distensible body portion connected to said non-distensible portion and adapted to be surgically implanted into the pendulous segment of said corpus cavernosum; and fluid supply means connected to said distensible body portion.

2. A penile prosthesis as in claim 1 wherein said non-distensible portion is made of a semi-rigid plastic material.

3. A penile prosthesis as in claim 2 wherein said plastic material is Silastic rubber.

4. A penile prosthesis as in claim 1 wherein said non-distensible portion is formed unitary with said distensible body portion.

5. A penile prosthesis as in claim 1 wherein said distensible body portion is adhesively bonded to said non-distensible portion.

6. A penile prosthesis as in claim 1 wherein said distensible body portion is an elongated, flexible tubular member having a thickened patch at the free end thereof.

7. A penile prosthesis as in claim 1 wherein said fluid supply means includes a fluid reservoir and a conduit connecting said fluid reservoir with said distensible body portion, and further including valve means disposed in said tubing for controlling the flow of fluid between said reservoir and said distensible body portion.

8. A penile prosthesis as in claim 7 wherein said tubing extends into the interior of said distensible body portions, and portion, a plurality of openings for facilitating the passage of fluid to and from said distensible body portion.

9. A penile prosthesis as in claim 1 wherein two non-distensible portions respectively connected to two distensible body portions are provided to be respectively implanted within the two corpora cavernosa of the penis, with each of said distensible body portions being connected to said fluid supply means.

10. A penile prosthesis as in claim 9 wherein two said fluid supply means are provided, each respectively connected to a distensible body portion of the penile prosthesis.

11. A penile prosthesis to be surgically implanted in a man comprising:
 a. two body portions, each adapted to be surgically implanted in a corpus cavernosum of the penis, each body portion including:
   a non-distensible part to be surgically implanted into the root of the respective corpus cavernosum; and
   a distensible portion formed unitary with said non-distensible portion and adapted to be surgically implanted into the pendulous segment of said corpus cavernosum; and
 b. fluid supply means adapted to be surgically implanted in the scrotum, and connected to each of said distensible portions of said body portions.

12. A penile prosthesis as in claim 11 wherein said fluid supply means includes a reservoir, fluid conduit means interconnecting said fluid reservoir with each of said distensible portions; and valve means for controlling the flow of fluid between said reservoir and said distensible body portions.

13. A penile prosthesis as in claim 11 wherein said body portions are made of a Silastic material.

* * * * *